United States Patent

Tsuda

Patent Number: 5,876,337
Date of Patent: Mar. 2, 1999

[54] MAGNETIC RESONANCE IMAGING APPARATUS AND METHOD FOR CORRECTING THE INTENSITY OF THE STATIC MAGNETIC FIELD OF THE APPARATUS

[75] Inventor: Munetaka Tsuda, Mito, Japan

[73] Assignee: Hitachi Medical Corporation, Tokyo, Japan

[21] Appl. No.: 829,523

[22] Filed: Mar. 28, 1997

[30] Foreign Application Priority Data

Apr. 1, 1996 [JP] Japan .................................. 8-079112

[51] Int. Cl.$^6$ .................................................. A61B 5/055
[52] U.S. Cl. ........................ 600/410; 324/318; 324/320; 324/307; 324/309
[58] Field of Search ..................... 324/307, 309, 324/318, 320; 600/410, 421

[56] References Cited

U.S. PATENT DOCUMENTS

| | | | |
|---|---|---|---|
| 4,425,547 | 1/1984 | Sugimoto | 324/318 |
| 4,761,612 | 8/1988 | Holland et al. | 324/307 |
| 5,530,352 | 6/1996 | Kolem | 324/309 |
| 5,661,401 | 8/1997 | Ishikawa et al. | 324/320 |

*Primary Examiner*—Marvin M. Lateef
*Assistant Examiner*—Eleni Mantis Mereader
*Attorney, Agent, or Firm*—Pennie & Edmonds LLP

[57] ABSTRACT

An MRI apparatus has a plurality of shim coils 102 and gradient magnetic field coils 104, which are connected to power sources 103 and 105 respectively. These power sources are controlled by a computer 112 to correct intensity of a static magnetic field generated by a magnet. For this purpose, the power sources 103 and 105 supply composite current of DC and AC so that the shim coils and the gradient magnetic field coils generate a rotating magnetic field. As a result, the uniformity of the static magnetic field in a region of an object under examination is improved and image distortion is suppressed. The MRI apparatus can be effectively applied to a fast imaging technique, an imaging technique where NMR signals of adipose tissue are suppressed, and a high resolution spectrum.

17 Claims, 7 Drawing Sheets

MAGNETIC RESONANCE IMAGING APPARATUS AND METHOD FOR CORRECTING THE INTENSITY OF THE STATIC MAGNETIC FIELD OF THE APPARATUS

BACKGROUND OF THE INVENTION

This invention relates to a magnetic resonance imaging apparatus and method using a nuclear magnetic resonance (hereinafter referred to as "NMR") phenomenon to obtain an NMR spectrum or tomographic image of a desired inner region of an object under examination non-invasively. In particular, it relates to a method for obtaining a substantially high uniformity of a static magnetic field in the apparatus.

The magnetic resonance imaging (hereinafter referred to as "MRI") apparatus uses an NMR phenomenon to obtain an NMR spectrum or tomographic image of a desired inner region of an object under examination non-invasively.

An object to be examined is placed in a uniform static magnetic field generated by a permanent magnet or a superconductive magnet. A high frequency magnetic field with a frequency equal to that of the Larmor precession (Larmor frequency $\omega$) of a specified atom, e.g., hydrogen (proton), constituting tissues of the object (e.g., human body) is applied to excite the nuclear spins and NMR signals emitted from the excited spins are measured as free induced decay or spin echo signals when the spins return to the ground state. Here, the Larmor frequency $\omega$ is calculated by the following formula and depends on the intensity of the magnetic field.

$$\omega = \gamma \cdot Ho$$

In the above equation, $\gamma$ is a magnetic rotational ratio inherent in each atomic nuclei. Ho is the intensity of the static magnetic field.

In ordinary MRI, gradient magnetic fields are superimposed on the static magnetic field to produce spatial difference in the magnetic field and a measuring sequence is repeated at a predetermined repetition time TR while adding location information to the NMR signals, thereby obtaining a plurality of NMR signals required for an image of one slice or spectrum. The static magnetic field in such MRI is required to be highly uniform in order to obtain high spatial resolution with a small gradient magnetic field.

Figure 7:
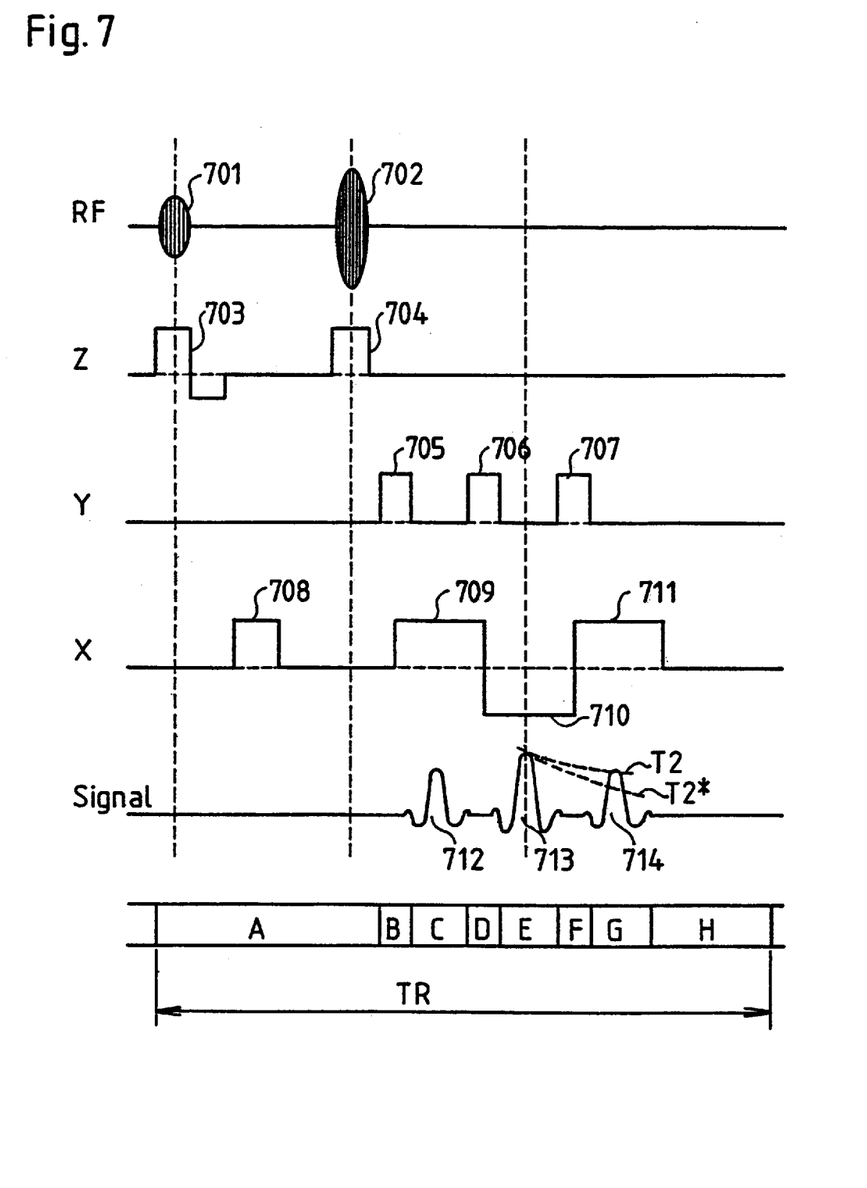
FIG. 7 is a timing chart of an MRI pulse sequence to which the present invention is applied.

Recently, fast imaging techniques have been developed and applied to clinical applications including a technique in which a plurality of echo signals with different phase encodes are measured within a single repetition time (JPA No.60-42906) or echo planer imaging (EPI) in which all of the phase encoded signals required for one image are measured at single excitation of the spins. These fast imaging techniques require still higher uniformity of the static magnetic field. As shown in FIG. 7, in the fast imaging technique in which the numbers (n) of echo signals are generated by switching the polarity of a readout gradient magnetic field and added with different phase encodes, the number n depends on decay characteristic of the signals. The phenomenon of an excited spin returning to its original state is called "relaxation" and when the nuclear spins are assumed to be macroscopic magnetization, relaxation in which the longitudinal magnetization component is in accord with the direction of the static magnetic field is called "longitudinal relaxation" and relaxation in which the lateral magnetization component is zero is called "lateral relaxation (T2 relaxation)." The relaxation rate of the T2 relaxation becomes rapid if the uniformity of the static magnetic field is bad. The relaxation occurring in a non-uniform static magnetic field is called "effective lateral relaxation (T2*)." When the effective lateral relaxation rate is rapid, the number n of echo signals measured at a single excitation is limited. Therefore, in order to measure more echo signals at a single excitation, the effective lateral relaxation rate should be slow, that is, the static magnetic field should have high uniformity.

Apart from this, a technique has been developed in which protons of adipose tissue are selectively saturated using the fact that resonance frequency $\omega'$ of protons of adipose tissue differs from that $\omega$ of protons of the other tissue (mainly water molecules). In this technique, since the difference between the resonance frequencies ($\omega'-\omega$) is approximately 4 ppm, the value of uniformity of the static magnetic field must be better than 4 ppm. However, it has been difficult to attain uniformity of this order for every examined object and, as a result, the signals from adipose tissue are not sufficiently suppressed in some cases.

To meet the requirement for the high uniformity of the static magnetic field, a conventional MRI apparatus is provided with shim coils for generating correcting magnetic field between the magnet for the static magnetic field and the coils for generating the gradient magnetic field. The shim coils consist of a combination of a plurality of coils such as X, Y. Z, $X^2$, $Y^2$. $Z^2$ ..., which correct local deviation of the static magnetic field. The uniformity of the static magnetic field, which is several ppm/40 cmdsv for a superconductive coil having high uniformity, is improved to some extent (around 1 ppm) by incorporating a plurality of shim coils.

A technique for separating protons of fatty acid group from those of hydroxy group of water using chemical shift ($\delta$) information included in NMR signals (spectroscopic imaging) has been developed and utilized for diagnosis of specific diseases (see, for example, JP No7-51124, J. Japan Magnetic Resonance Medical Science "Quantitative measurement of adipose using chemical shift imaging—Study on Duchenne-type muscular dystrophy" issued 1991). Since the proton chemical shift usually ranges around 7 ppm (maximum 20 ppm), a uniformity of the static magnetic field of better than 7 ppm is required. However, as mentioned above, the conventional MRI apparatus with shim coils achieves uniformity of only several ppm and thus chemical shift information of higher resolution can not be utilized.

Further, when a human body is the object to be examined, the rate of magnetization varies from place to place depending on the difference of tissues, blood or gases in the coelome or the like. This variation in the rate of magnetization leads to local changes in the uniformity of the applied static magnetic field. This variation can not be corrected by the shim coils, because it occurs locally. Thus, use of high-resolution spectrum has been severely limited in medial diagnosis.

On the other hand, the NMR spectrometer utilized for measuring high resolution spectrum in the field of analytical chemistry is provided with shim coils of various shapes, which are applied with an electric current to generate a magnetic field for correcting the ununiformity of magnetic field of the space where the samples are placed. Uniformity of the magnetic field ranging $10^{-7} \sim 10^{-8}$ can be obtained by the shim coils. In addition, the samples are subjected to high speed rotation so that all of the spins in the samples are subjected to an average of the uneven magnetic field intensity. This improves the substantial uniformity of the magnetic field in the samples to a level of $10^{-9}$(0.001 ppm) and enables a high resolution spectrum to be obtained.

However, this method can not be applied to an MRI apparatus where the object to be examined is a human body, while rotation of the magnet or shim coils can not be realized because of their weight.

SUMMARY OF THE INVENTION

An object of the present invention is to provide an MRI apparatus and method which improve substantially the uniformity of the static magnetic field in a human body and reduce image distortion. Another object of the present invention is to provide an MRI apparatus to which the fast imaging techniques can be applied. Another object of the present invention is to provide an MRI apparatus which realizes a substantially improved uniformity of the static magnetic field in a human body and is applicable for imaging techniques wherein the signals of adipose tissue are effectively suppressed. Another object of the present invention is to provide an MRI apparatus which substantially improves the uniformity of the static magnetic field in a human body and with which a high resolution spectrum for diagnosis is obtainable.

In order to achieve the above object, the MRI apparatus of the present invention, for obtaining diagnostic information by utilizing the magnetic resonance phenomenon and measuring an inner region of the object to be examined, comprises means for generating a uniform static magnetic field in a space where an object to be examined is placed, means for generating gradient magnetic fields with different intensity depending on the position in the space, correcting means for generating a magnetic field for correcting the uniformity of the static magnetic field generated by the static magnetic field generating means, means for generating a high frequency magnetic field for exciting nuclear spins of the object to be examined, detecting means for detecting nuclear magnetic resonance signals of the spins, means for processing and computing the detected magnetic resonance signals and for displaying the computed results and means for varying the relative position of the correcting magnetic field generated by the correcting means and the object under examination. In the present invention, the correcting magnetic field may be generated by either the correcting means or means for generating the gradient magnetic field. The term "correcting magnetic field generating means" used here includes both means.

To vary the positional relationship between the correcting magnetic field and the object under examination, a rotational magnetic field is generated. More precisely, the correcting magnetic field generating means comprises a plurality of magnetic field generating coils, to which composite current consisting of direct current (DC) and alternating current (AC) is applied. Rotating the correcting magnetic field causes a similar effect to rotating the object under examination and enables establishment of a highly uniform static magnetic field in the object (human body). Further, since the rotating magnetic field is formed electrically, it can rotate on a desired axis or at a desired point tridimensionally to produce a static magnetic field of higher uniformity, whereas that of the NMR spectrometer can rotate only on the specified axis.

In a more specific embodiment according to the present invention, in order to produce the rotational correcting magnetic field, a power source circuit for driving the correcting magnetic field generating means comprises means for outputting AC having a predetermined wave form, means for outputting predetermined DC to the plurality of the magnetic field generating coil and means for modulating the DC with the AC for application to the magnetic field generating coils. This power circuit may be an analog circuit or a digital circuit. However, the latter is advantageous because it is easy to control and does not phase lock. The means for outputting the AC having the predetermined wave form may be a function generator which generates a desired wave form, for example a sine wave.

According to the MRI method of the present invention, in the process of placing the object to be examined in a uniform static magnetic field, applying the high frequency magnetic field, pulsewise applying the gradient magnetic fields for slice selection, phase encoding and readout according to a predetermined sequence to cause NMR in the region of concern of the object, and detecting the signals based on the NMR to obtain an image or NMR spectrum of the region of concern, the uniformity of the static magnetic field is adjusted at every step of placing the object to be examined and positional relationship between the correcting magnetic field generated by this adjustment and the object under examination is varied at least during acquisition of NMR signals. More precisely, a) a correcting magnetic field of at least two axial directions is superimposed on the static magnetic field and an optimal intensity of the correcting magnetic field for making the static magnetic field uniform is determined, b) the object to be examined is placed in the space of the static magnetic field and the correcting magnetic field of determined intensity is applied as a rotating magnetic field, c) an optimal condition of the rotating correcting magnetic field for making the static magnetic field uniform is determined, and d) a predetermined sequence is performed while applying the rotating correcting magnetic field under the determined condition.

The step a) is carried out by placing a homogenous sample such as water in the space of the static magnetic field and measuring NMR signals therefrom. This step need not be conducted often because the static magnetic field generating means, i.e., the magnet itself, is relatively stable. The steps from b) on are conducted every time the object to be examined is changed. In the step b), AC signals of several kHz are applied to the power source of the correcting magnetic field generating means to form the rotational magnetic field and in the step c), the amplitude of the AC signals is varied and an optimum amplitude is determined so that an optimum correcting magnetic field can be obtained. The optimum condition can be determined by measuring NMR signals and thus a high uniformity of the static magnetic field which is adjusted to the object under examination can be formed in the human body.

Further, a method of the present invention for correcting intensity of static magnetic field of an MRI apparatus comprises a) step of superimposing a correcting magnetic field of at least two axial directions on the static magnetic field and determining an optimal intensity of the correcting magnetic field for making the static magnetic field uniform, b) step of placing the object to be examined in the space of static magnetic field and applying the correcting magnetic field of the determined intensity as a rotating magnetic field, and c) step of determining an optimal condition of the rotating correcting magnetic field for making the static magnetic field uniform.

The correcting magnetic field is preferably a rotating magnetic field which is generated by applying composite direct and alternating current to a plurality of magnetic field generating coils.

Further, in the method according to the present invention, the step of determining an optimal correcting magnetic field intensity for making the static magnetic field uniform further comprises: 1) step of placing a phantom in the static magnetic field, 2) step of applying a high frequency magnetic field to the phantom and detecting FID (free induced decay) signals caused thereby, 3) step of conducting Fourier transformation of the FID signals to obtain a spectrum, 4) step of finding a half width of the spectrum peak and 5) step of repeating the steps from 2) to 4) while changing the current value for correcting the magnetic field to obtain the amplitude of the AC applied to each of the plurality of magnetic field generating coils so that the half width becomes minimum.

According to the present invention, substantial uniformity of static magnetic field in the space where the object to be examined is present can be obtained by changing the position of the correcting magnetic field relative to the object under examination, thereby reducing distortion of the MRI image due to the ununiformity. In the fast imaging sequence using reversing gradient magnetic fields, results with high SN ratio can be obtained, since the effect of the ununiformity on decay of NMR signals obtained from the examined site of the object is reduced. In the technique where NMR signals of adipose tissue are suppressed, a high-quality image for protons can be obtained Further, a high resolution spectrum of the examined site of the object can be measured.

DESCRIPTION OF THE PREFERRED EMBODIMENT

A preferred embodiment of the present invention will be explained hereinafter with reference of the drawings.

Figure 1:
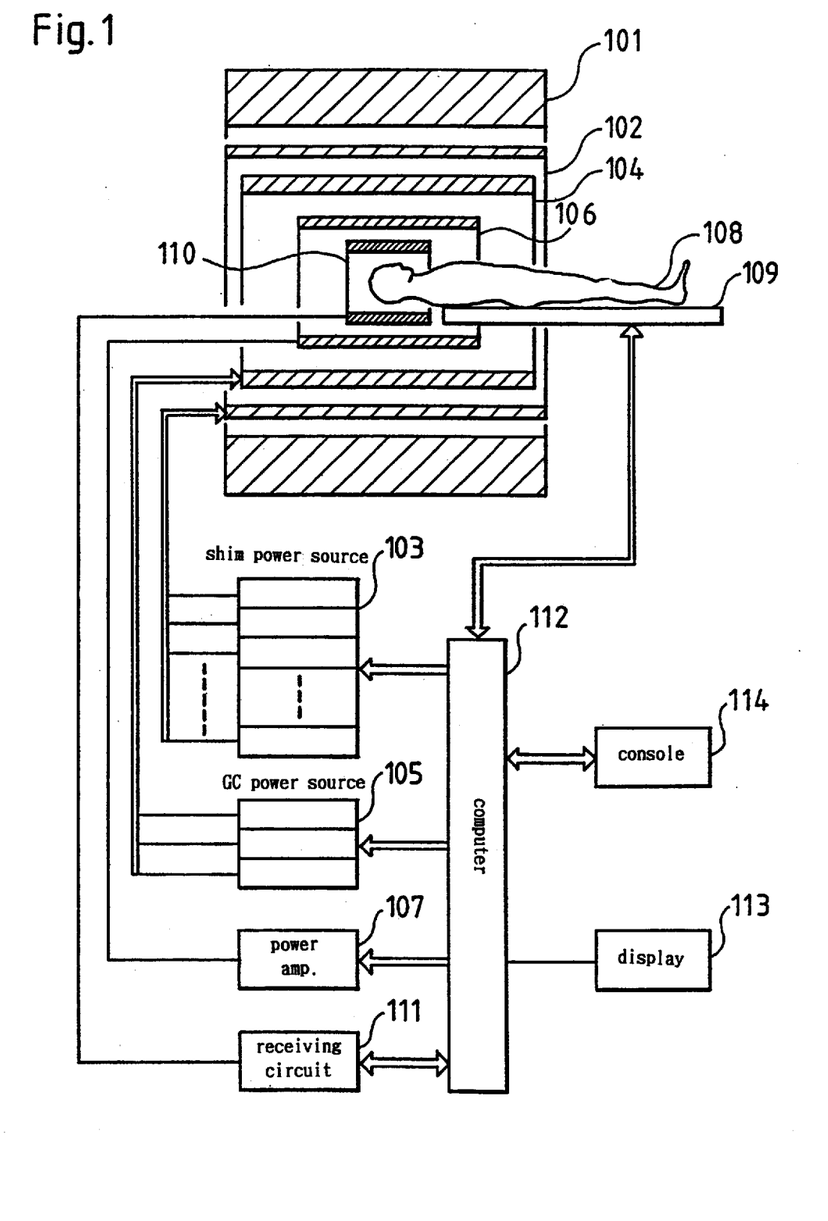
FIG. 1 is a schematic view of a preferred embodiment of an MRI apparatus to which the present invention is applied.

FIG. 1 is a diagram of an MRI apparatus which is a preferred embodiment of the present invention. This MRI apparatus is provided with a magnet 101 as the static magnetic field generating means. The bore of the magnet 101 is incorporated with shim coils 102 for correcting the static magnetic field generated by the magnet 101, gradient magnetic field generating coils (hereinafter referred as gradient coils) 104 for generating gradient magnetic fields superimposed on the static magnetic field and a high frequency coil 106 which generates a high frequency magnetic field to excite nuclear spins of the region to be examined of the object 108.

As the magnet 101, a permanent magnet, a resistive magnet or a superconductive magnet (hereinafter referred to as SCM) can be employed. The exemplified apparatus is equipped with a SCM constituted of superconductive wire wound as a solenoid in a container having an outer diameter of 2 meters, inner diameter of 1 meter and a length of 2 meters. This solenoid SCM typically has a magnetic field intensity of 1.5 tesla and a uniformity of 5 ppm in a spherical space of 40 cm in the central part of the bore.

The shim coils 102 consist of a plurality of coils such as X, Y and Z coils each of which imparts the first order correction of the static magnetic field in three axial directions X, Y and Z, $X^2$, $Y^2$ and $Z^2$ coils each of which imparts second order correction, $X^3$, $Y^3$ and $Z^3$ coils each of which imparts third order correction, and first order correction coils for correction in the XY, YZ and XZ directions. For example, coils having a shape similar to that of a known NMR spectrometer but of a larger size can be used. Generally, the shim coils comprise 9 to 12 kinds of coils, except for the X Y, Z coils which also function as the gradient coils. A bobbin on which the shim coils are wound or to which the pattern of the coils is fixed is incorporated inside the magnet bore. Each of the shim coils 102 is connected to a power source circuit 103 to be supplied with current independently. A constant current is supplied to the coils so as to improve the uniformity of the static magnetic field in the central space of the magnet bore. A method for adjusting the current will be explained later.

The gradient coils 104 consist of three coils for three directions X Y and Z. Each of coils is fixed to a bobbin and incorporated inside the shim coils 102. Power sources 105 are connected independently to these gradient coils 104 and apply the coils with current for improving the uniformity of the magnetic field and pulse current for encoding position information to NMR signals from the examined region of the object.

Both of the power sources 103, 105, for the shim coils 102 and the gradient coils 104, have sufficient current capacity to correct the uniformity of the magnetic field of the space where a human body is placed (40 cm/dsv) and stability. Further, they are provided with means for generating rotating magnetic field as described later. These coils and the power source are arranged not to interact.

The high frequency coil 106 has a specific resonance characteristic for exciting nuclear spins of the examined region of the object. For example, if the intensity of the magnetic field is 1.5 tesla and the objective nucleus is hydrogen nucleus, the resonance characteristic is 64 MHz. A high frequency power amplifier 107 of, for example, about 20 KW, is connected to the high frequency coil 106 so that it generates a high frequency magnetic field with an intensity sufficient to excite nuclear spins.

The object 108 to be examined is placed laterally on the patient table 109 and a high frequency coil 110 for detecting NMR signals is placed near the examined region of concern and carried into the central space of the magnet. A receiving circuit 111 for amplifying and detecting the NMR signals is connected to the high frequency coil 110.

The shim power source 103, the gradient coil power sources 105, the high frequency power amplifier 107 and the receiving circuit 111 are connected to a computer 112. The computer 112 generates signals for controlling the operation of the above units and processes the detected NMR signals to transform them for the purpose of diagnosis. An operator's console 114 for operating the apparatus is connected to the computer 112. The above units are essential components of the MRI of the present invention.

Further, the MRI of the present invention is provided with a function generator and a modulator, which are incorporated in the power sources 103 and 105 as means for giving an electrical rotation to the correcting magnetic field generated by the shim coils and the gradient coils.

Figure 2:
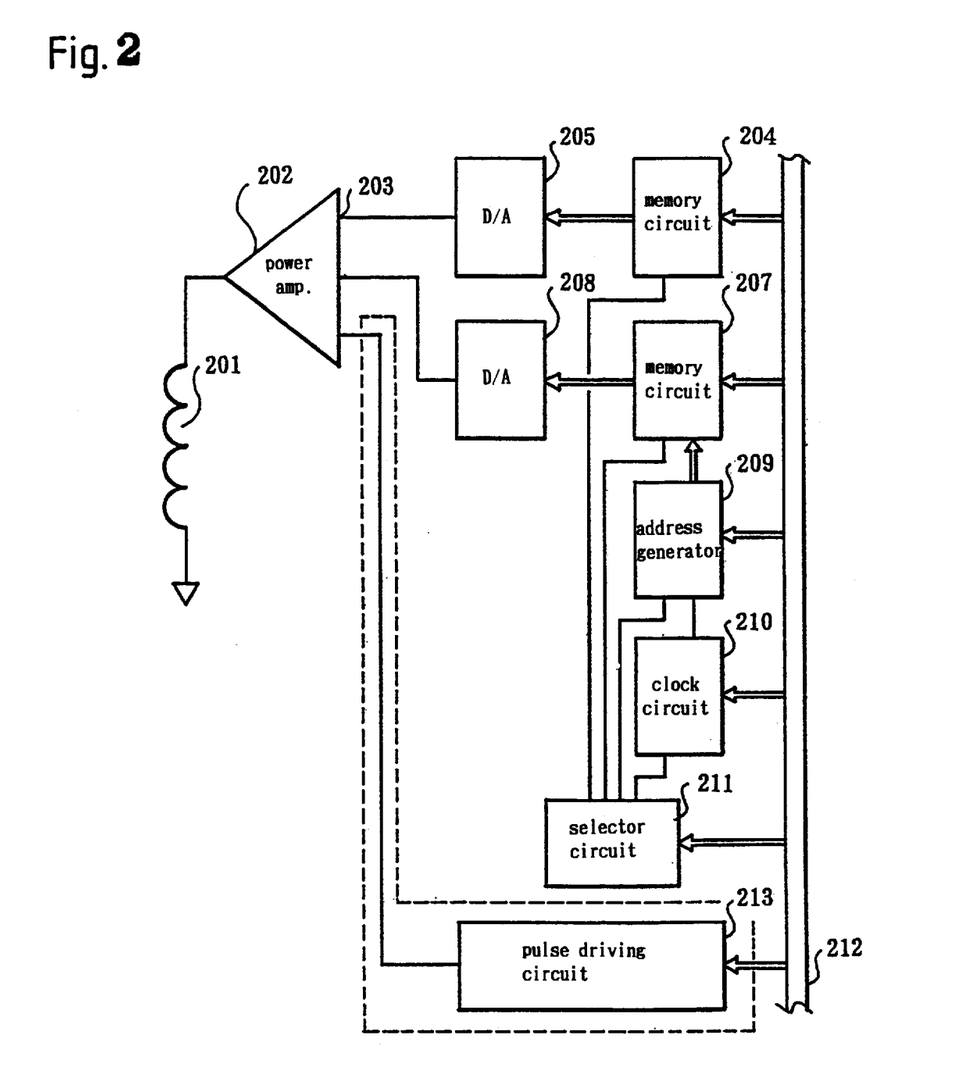
FIG. 2 is a diagram showing an MRI apparatus according to the present invention.

One embodiment of the shim coil power source is shown in FIG. 2. In the drawing, the portion enclosed by a dotted line is a pulse driving circuit, which is required if this power source is that of the gradient coils. It is not necessary if the power source is that of the shim coils.

This power source circuit has two memory circuits 204, 207 each of which is connected to the function generator (not shown) and the computer 112 through a data bus 212, a clock circuit 210 for determining the timing when the memory circuit reads data from the data bus 212 and a selector circuit 211 which selects one of the memory circuits to which the data from the bus is written. The memory circuits 204, 207 are connected to D/A converters 205, 208 respectively. The A/D converters convert the data output from the memory circuits and forward them to a power amplifier 202 which modulates them. The output of the power amplifier 202 is connected to the shim coil 201.

The current value for correcting the uniformity of the static magnetic field, which is computed by the computer 112 using an adjustment process described later, is input to one memory circuit 204 through the selector circuit 211 and this current value is converted to a constant voltage by the D/A converter 205 and sent to one input terminal 203 of the power amplifier 202.

Data sent from the function generator through the selector circuit 211, for example a sine wave of one cycle, is written in the other memory circuit 207. The D/A converter 208 outputs the data as a sine wave voltage signal. The frequency of this AC signal may be several kHz and the amplitude thereof is determined by the adjustment process described later. The current amplifier adds the constant voltage and the sine wave voltage are applied to the two input terminals and supplies a current corresponding to these voltages to the coil 201. This means that a portion of the correcting current is transformed by the wave form generated by the function generator.

When the data written in the memory circuit 207 is read out successively, the read out timing is synchronized to timing pulses generated by the clock circuit 210 and the length of the sine wave cycle can be varied based on the interval of the timing pulses of the clock circuit 210. Further, an address generator 209 is connected to the memory circuit 207 to control the phase of the sine wave by the output signal of the address generator. Therefore, instead of outputting a sine wave voltage as explained here, it is possible, for example, to output a cosine wave voltage from the other coil. Thus, for example, the X-direction on coil can be modulated with sine wave $\omega$ and the Y-direction coil can be modulated with cosine wave $\omega$ so that the composite magnetic field generated by the two gradient coils rotates with angular velocity $\omega$.

The configuration of the shim power source is explained in the foregoing. If the power source is that of the gradient coils, the pulse driving circuit 213 enclosed by the dotted line is added thereto. The output from the pulse driving circuit 213 is mixed with both the constant voltage and the voltage changing with sine wave and applied to the gradient coil.

A power source composed of digital circuits is exemplified in FIG. 2, but it can be composed of any kind of circuits capable of modulating the DC component of the correcting magnetic field to AC, e.g., analog circuits. However, a digital circuit configuration is advantageous since it does not phase lock and facilitates control. The wave form generated by the function generator is not limited to a sine wave.

Figure 4:
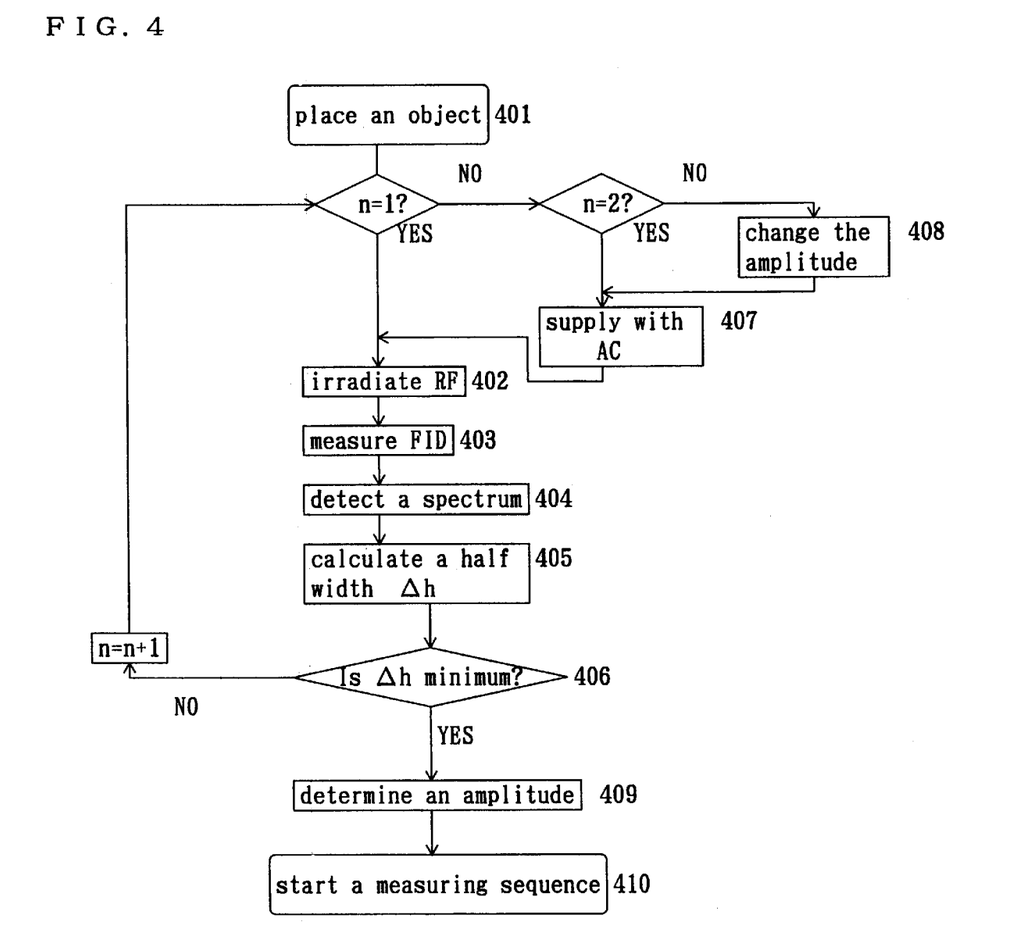
FIG. 4 is a timing chart of a pulse sequence for adjusting the correcting magnetic field in one embodiment of the present invention.
Figure 5:
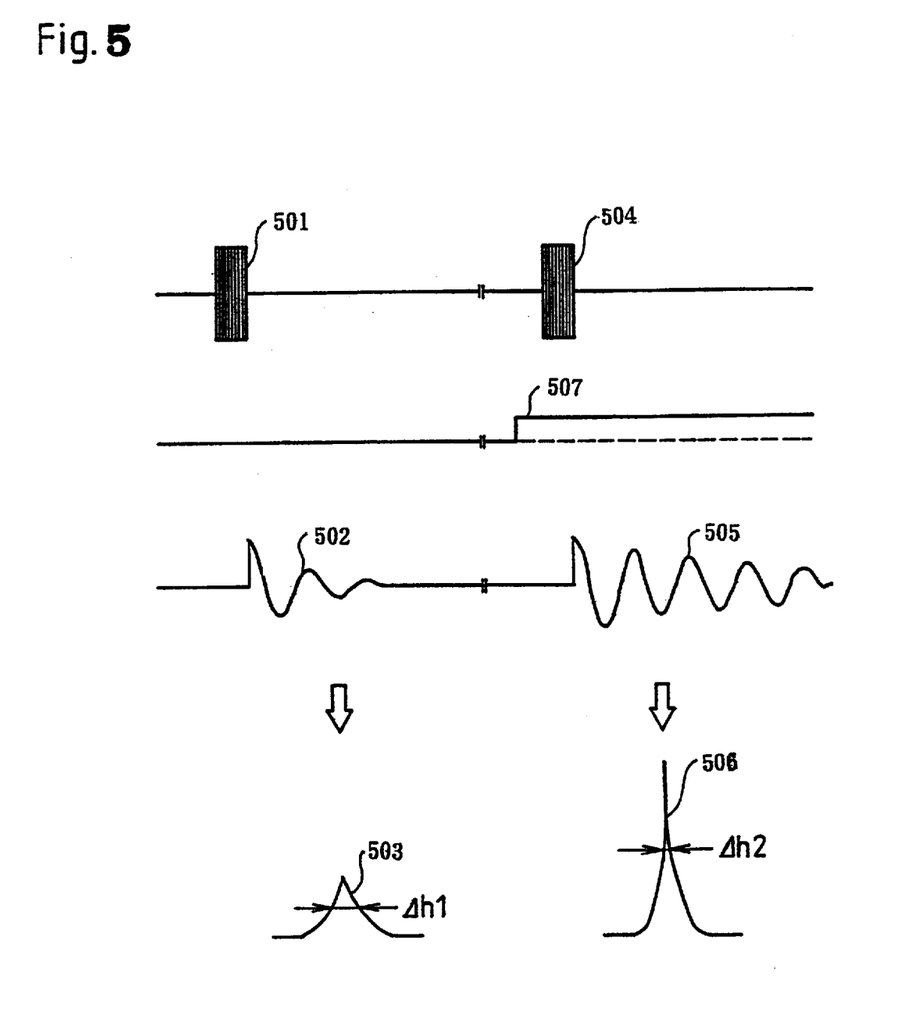
FIG. 5 is a flowchart of adjustment of the correcting magnetic field during MRI in one embodiment according to the present invention.

Operation of the MRI apparatus having the above-mentioned constitution will be explained hereinafter with reference of the flowcharts of FIGS. 3, 4 and the timing charts of FIGS. 5, 6.

Figure 3:
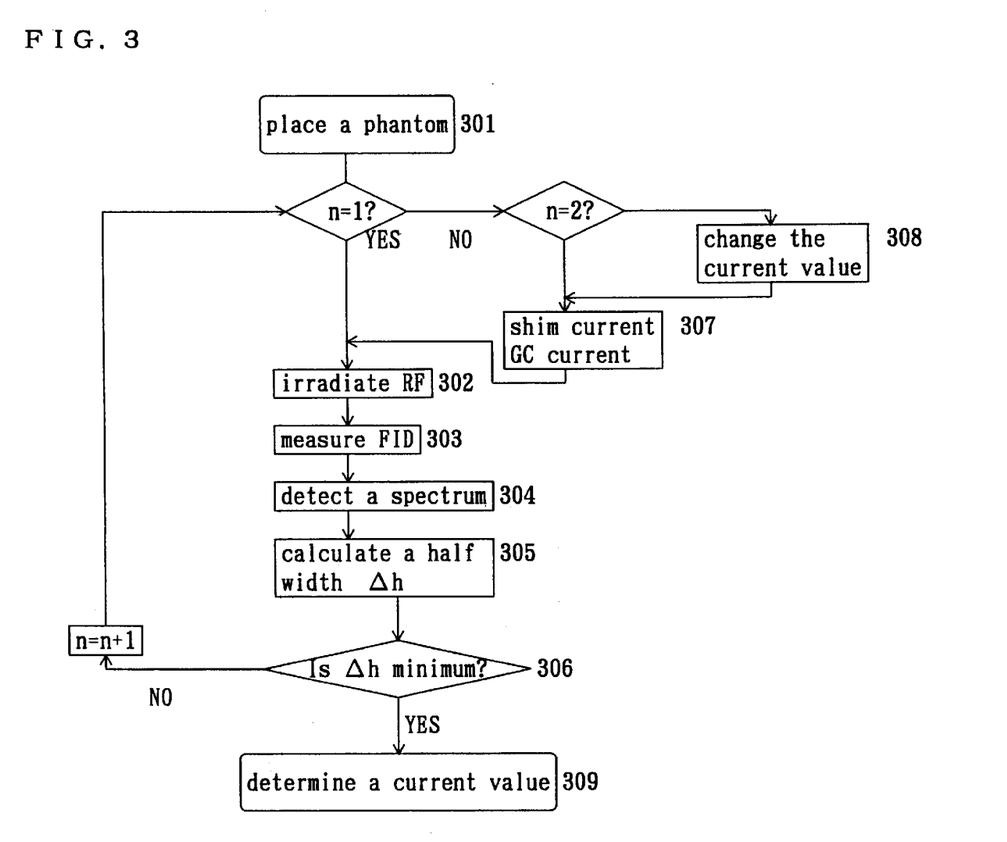
FIG. 3 shows a flowchart of adjustment of the correcting magnetic field in one embodiment according to the present invention.

First, the uniformity of the magnet is adjusted by changing currents of the shim coils and the gradient coils (see flowchart of FIG. 3). For this purpose, a phantom sample is placed in the central part of the magnet 101 (301) instead of the object to be examined. As the phantom, a spherical sample of a diameter of 20 cm in which protons are dispersed homogeneously can be employed. In this situation, the output of the high frequency power source is applied to the high frequency coil 106 so that rectangular high frequency magnetic field pulses 501 are generated (302). In this initial state (n=1), no correcting magnetic field is applied. After the high frequency magnetic field pulse 501 is applied, FID signal 502 is detected by the same high frequency coil 106. The FID signal 502 is amplified by the receiving circuit 11 and Fourier transformed by the computer 112 to obtain spectrum 503 (304). Then, a half width $\Delta$ h1 of the obtained spectrum peak is found (305). Next, correcting magnetic field is applied while current strengths of the shim power source 103 and the gradient coil power source 105 are varied (307, 308). Then the steps (303–305), i.e., applying RF magnetic field pulse 504, detecting FID signal 505 and calculating the half width of the obtained spectrum peak are repeated. The current strength for only one coil is shown in FIG. 5 but this operation is carried out for at least two coils and the current strength at which the half width becomes minimum (306, 309) is determined. The step for finding the minimum (306) may be performed by changing the current strength a predetermined numbers of times (n) and finding the least value of n values. Alternatively, the current value, when it becomes less than a threshold value, may be determined as the minimum. A known algorithm can be employed to determine the minimum value.

The reason why the half width is used as a measure of the uniformity of the magnetic field is that it corresponds to the decay characteristic of the FID signal. Generally, the decay characteristic of an FID signal includes two factors: the decay due to ununiformity of the magnetic field and the decay due to relaxation process of nuclear spins. When the uniformity of the magnetic field is good, the decay of the FID signal due to the relaxation of nuclear spins is predominant and the half width becomes narrow. Therefore, the uniformity of the magnetic field can be optimized by finding and comparing the half wave length successively while changing the current value.

In the last of this adjustment operation, both the shim power source and the gradient coil power source are controlled by computer so that the currents are constantly applied to the coils (307). This operation need not to be carried out frequently since the uniformity of the magnet is relatively stable. It may be carried out when the apparatus is installed or at monthly inspection of the apparatus as a readjustment procedure.

The uniformity of the magnet of the thus-adjusted MRI apparatus is highly improved but, as pointed out earlier, ideal magnetic field can not be attained. In actual measurement, the object under examination has an effect on the static magnetic field and causes complicated distribution of the magnetic field. Therefore, the correcting magnetic field generated by the shim coils and the gradient coils is rotated by electrical means in the actual measurement.

The flow of the actual measurement will now be explained. At first, an object 108 to be examined (human body) is placed in the center of the magnet 101 (FIG. 4 (401)). In this situation, as shown in FIG. 6, the output of the high frequency power source 107 is applied to the high frequency coil 106 so that rectangular high frequency magnetic field pulses 601 are generated (402). After the high frequency magnetic field pulses 601 are applied, an FID signal 602 is detected by the detector high frequency coil 110 (403). The FID signal 602 is amplified by the receiving circuit 11 and Fourier transformed by the computer 112 to obtain a spectrum 603 (404). Then, a half width Δ h3 of the obtained spectrum peak is found (405). Next, while superimposing an AC signal on each of the adjusted current values of the shim coil power sources and the gradient coil power sources (407), which have been set according to the flowchart (309) of FIG. 3, and changing the amplitude of the AC signal 604 (408), the steps (402–406) of applying RF magnetic field pulses 605, detecting the FID signal 606 and calculating the half width Δh4 of the obtained spectrum peak 607 are repeated.

Figure 6:
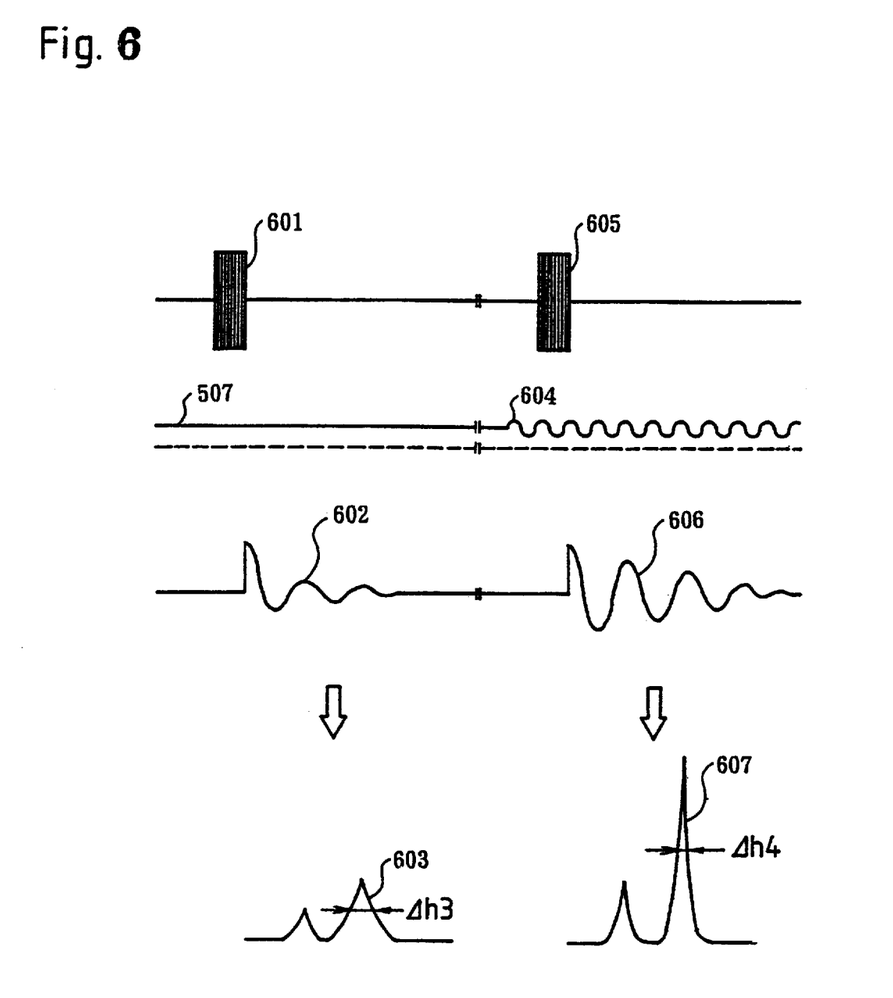
FIG. 6 is a timing chart of a pulse sequence for adjustment of the correcting magnetic field of FIG. 5.

The current strength for only one coil is shown in FIG. 6 but this operation is carried out for shim coils and/or gradient coils of at least two directions. Actually, by rotating the first order correcting magnetic field of the X, Y, Z coils, the desired uniformity can be attained for the most part.

The spectra 603, 607 obtained by the sequence of FIG. 6 has a plurality of peaks depending upon the examined part of the object unlike the homogeneous sample. In this case, the half width of a specific peak, e.g. a peak having the maximum amplitude or an average of the all peaks can be used for the calculation. By finding and comparing the half width successively while changing the AC signal 604, the uniformity of the magnetic field of the examined part of the object can be optimized substantially.

In the last of this adjusting operation, both the shim power source and the gradient coil power source are controlled by the computer 112 so that the currents are constantly applied to the coils (409). After the above-mentioned adjustment is completed, an imaging pulse sequence in accord with the purpose of measurement is started (410). That is, a sequence of fast imaging or high resolution spectrum measurement is effected.

Measurement of the head of the object (human body) 108 using the fast imaging technique will be explained with reference of FIG. 7. During the section A of FIG. 7, 90° high frequency pulse 701 and 180° high frequency pulse 702 are irradiated onto the examined region in the presence of the gradient magnetic fields Z 703 ,704 to obtain a spin echo signal of the region. During the section E, when twice the time between 90° RF pulse 701 and 180° RF pulse 702 has passed, the spin echo signal is generated. Further, during the section C, the gradient echo signal 712 is generated by the reversed gradient magnetic field X pulses 708, 709 and during the section G, the gradient echo signal 714 is generated by the reversed gradient magnetic field X pulses 710, 711. These gradient echo signals decay with T2* depending upon the uniformity of the magnetic field and in the case of high uniformity of the magnetic field, the decay characteristic becomes close to the relaxation time T2 curve. As a result, these gradient echo signals have a good S/N and, similarly to spin echo signals, can be utilized as matrix data of an image. Prior to the acquisition of echo signals, during the sections B, D and F, gradient magnetic field Y pulses 705, 706 and 707 for phase encoding are applied. The gradient echo signal 712 is encoded by the phase encoding pulse 705, the gradient echo signal 713 is encoded by the phase encoding pulses 705 and 706 and the gradient echo signal 714 is encoded by the phase encoding pulses 705, 706 and 707. Namely, three encoded NMR signals are measured within the repeating term TR (from the section A to the retaining (waiting) term D) and thus the measurement can be completed in a third of the usual imaging time.

In the present invention, EPI or the like can be applied as an imaging sequence instead of the above-mentioned gradient spin echo imaging and matrix data with high S/N can be obtained. Further, the present invention can be effectively applied to the imaging in which NMR signals from adipose tissue are suppressed and to spectroscopic imaging.

I claim:

1. A magnetic resonance imaging (MRI) apparatus comprising:

means for generating a uniform static magnetic field in a space where an object to be examined is placed;

means for generating a gradient magnetic field whose intensity depends on the location within the space;

means for generating a correcting magnetic field that corrects the static magnetic field;

means for generating a high frequency magnetic field for exciting nuclear spins within said object;

means for detecting nuclear magnetic resonance signals from said spins;

means for processing and computing the detected magnetic resonance signals and for displaying the computed results; and means for moving the correcting magnetic field relative to the object to further correct the static magnetic field corrected by the means for generating a correcting magnetic field.

2. The MRI apparatus according to claim 1, wherein the means for generating the correcting magnetic field further comprises means for rotating the correcting magnetic field to vary the position of the correcting magnetic field relative to the object under examination.

3. The MRI apparatus according to claim 1, wherein the means for generating the correcting magnetic field comprises a plurality of magnetic field generating coils and power sources for supplying composite current of direct current and alternating current to each of the magnetic field generating coils.

4. The MRI apparatus according to claim 3, wherein the power source(s) comprises means for outputting alternating current having a predetermined wave form and means for outputting predetermined direct current to the plurality of the magnetic field generating coils and means for modulating the direct current with the alternating current and applying it to each of the magnetic field generating coils.

5. Method for obtaining an image or NMR spectrum of a region of an object to be examined by placing the object to be examined in a uniform static magnetic field, applying a high frequency magnetic field(s) and gradient magnetic fields for slice selection, phase encoding and readout to the object according to a predetermined sequence, causing magnetic resonance in the region and detecting signals based on the magnetic resonance, which comprises the following steps:

a) superimposing a correcting magnetic field of at least two axial directions on the static magnetic field and determining an optimal correcting magnetic field for making the static magnetic field uniform, b) placing the object to be examined in a space of the static magnetic field and applying the determined correcting magnetic field as a rotating magnetic field, c) determining an optimal condition of the rotating correcting magnetic field for making the static magnetic field uniform, and d) performing the predetermined sequence while applying the rotating correcting magnetic field under the determined condition.

6. Method for correcting intensity of a static magnetic field of a magnetic resonance imaging apparatus, which comprises the following steps:
   a) superimposing a correcting magnetic field of at least two axial directions on the static magnetic field and determining an optimal correcting magnetic field for making the static magnetic field uniform,
   b) placing the object to be examined in a space of the static magnetic field and applying the determined correcting magnetic field as a rotating magnetic field, and
   c) determining an optimal condition of the rotating correcting magnetic field for making the static magnetic field uniform.

7. The method according to claim 6, wherein the rotating magnetic field is generated by applying composite current of direct current and alternating current to a plurality of magnetic field generating coils.

8. The method according to claim 6, wherein the step of determining the optimal correcting magnetic field further comprises;
   1) placing a phantom in the static magnetic field,
   2) applying a high frequency magnetic field(s) to the phantom and detecting FID signals generated thereby,
   3) conducting Fourier transformation of FID signals to obtain a spectrum,
   4) finding a half width of the spectrum peak,
   5) repeating the steps from 2) to 4) to find the amplitude of the alternating currents applied to each of the plurality of magnetic field generating coils at which the half width becomes minimum while changing the current value for the correcting magnetic field.

9. The MRI apparatus according to claim 1 wherein said means for moving the correcting magnetic field relative to the object, is provided during application of the high frequency magnetic field for exciting nuclear spins within the object and detection of nuclear magnetic resonance signals from the spins.

10. The MRI apparatus according to claim 1, wherein said means for generating the correcting magnetic field includes the means for generating gradient magnetic field.

11. The MRI apparatus according to claim 1, wherein said means for generating the correcting magnetic field includes the means for moving the correcting magnetic field relative to the object under examination.

12. The MRI apparatus according to claim 11, wherein the means for generating the correcting magnetic field comprises a plurality of magnetic field generating coils and power sources for supplying composite current of direct current and alternating current to each of the magnetic field generating coils.

13. A magnetic resonance imaging (MRI) apparatus, comprising:
   means for generating a uniform static magnetic field in a space where an object to be examined is placed;
   means for generating a gradient magnetic field whose intensity depends on the location within the space;
   means for generating a correcting magnetic field that corrects the static magnetic field;
   means for generating a high frequency magnetic field for exciting nuclear spins within said object;
   means for detecting nuclear magnetic resonance signals from said spins;
   means for processing and computing the detected magnetic resonance signals and for displaying the computed results; and
   means for smoothing the ununiformity of the corrected static magnetic field by moving the correcting magnetic field with respect to time and space relative to the object under examination.

14. A magnetic resonance imaging (MRI) apparatus, comprising:
   means for generating a uniform static magnetic field in a space where an object to be examined is placed;
   means for generating a gradient magnetic field whose intensity depends on the location within the space;
   means for generating a correcting magnetic field that corrects the static magnetic field;
   means for generating a high frequency magnetic field for exciting nuclear spins within said object;
   means for detecting nuclear magnetic resonance signals from said spins;
   means for processing and computing the detected magnetic resonance signals and for displaying the computed results; and
   means for controlling the correcting magnetic field so as to correct the static magnetic field corrected by the means for generating the correcting magnetic field.

15. A magnetic resonance imaging (MRI) apparatus comprising:
   a magnet(s) (magnetic circuit) for generating a uniform magnetic field in a space where an object to be examined is placed;
   a plurality of coils placed within the space to generate a high frequency magnetic field for exciting nuclear spins within the object, a gradient magnetic field whose intensity depends on the location within the space and a correcting magnetic field that corrects the static magnetic field;
   a detecting coil placed close to the object to detect nuclear magnetic resonance signals from the spins;
   an operating unit connected to the plurality of coils and the detecting coils to operate these coils;
   a computer (processing unit) connected to the operating unit to generate signals for controlling the operation of the operating unit and to input the magnetic resonance signals from the detecting coil for processing and computing; and
   a display connected to the computer for displaying the computed results;
   wherein the operating unit drives the plurality of coils to move the correcting magnetic field relative to the object so as to further correct the static magnetic field by the correcting magnetic field.

16. A method for obtaining magnetic resonance images or NMR spectrum, which comprises the following steps:
   a) placing an object to be examined in a static magnetic field,
   b) correcting the static magnetic field by generating a correcting magnetic field,
   c) producing nuclear magnetic resonance in a region of concern and detecting signals caused by the nuclear magnetic resonance and
   d) further correcting the corrected static magnetic field simultaneously with step c).

17. The method of claim 16, wherein the step d) comprises a step of moving the collecting magnetic field with respect to time and space relative to the object under examination to smooth the ununiformity of the corrected static magnetic field.

* * * * *